(12) United States Patent
Al-Majnouni et al.

(10) Patent No.: US 11,267,770 B2
(45) Date of Patent: Mar. 8, 2022

(54) PROCESS TO PRODUCE OLEFINS FROM A CATALYTICALLY CRACKED HYDROCARBONS STREAM

(71) Applicant: SABIC Global Technologies B.V., Bergen op Zoom (NL)

(72) Inventors: Khalid A. Al-Majnouni, Riyadh (SA); Ahmed Alzenaidi, Riyadh (SA); Nabil Al-Yassir, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 124 days.

(21) Appl. No.: 16/462,769

(22) PCT Filed: Dec. 14, 2017

(86) PCT No.: PCT/IB2017/057968
§ 371 (c)(1),
(2) Date: May 21, 2019

(87) PCT Pub. No.: WO2018/116091
PCT Pub. Date: Jun. 28, 2018

(65) Prior Publication Data
US 2019/0367432 A1    Dec. 5, 2019

Related U.S. Application Data

(60) Provisional application No. 62/437,306, filed on Dec. 21, 2016.

(51) Int. Cl.
*C07C 6/04* (2006.01)
*C07C 4/06* (2006.01)
(Continued)

(52) U.S. Cl.
CPC .............. *C07C 6/04* (2013.01); *C07C 4/06* (2013.01); *C07C 7/09* (2013.01); *C10G 63/04* (2013.01);
(Continued)

(58) Field of Classification Search
CPC ............. C07C 6/04; C07C 4/06; C10G 63/04
See application file for complete search history.

(56) References Cited

U.S. PATENT DOCUMENTS 3,723,561 A    3/1973 Priegnitz ................ 585/820
3,758,403 A *  9/1973 Rosinski et al. ........ B01J 29/80
                                                  502/67
(Continued)

FOREIGN PATENT DOCUMENTS

CN    1299341 A    6/2001
CN    1639091 A    7/2005
(Continued)

OTHER PUBLICATIONS

International Search Report and Written Opinion from PCT/IB2017/057968 dated Mar. 12, 2018, 11 pages.

*Primary Examiner* — Thuan D Dang
(74) *Attorney, Agent, or Firm* — Norton Rose Fulbright US LLP (57) ABSTRACT

Processes to produce olefins from a hydrocarbons stream obtained from a catalytic cracking unit are described. The process includes the integration of metathesis of $C_4$ olefin process and a hydrocarbon catalytically cracking process to produce commercially valuable products (for example, $C_{2-3}$ olefins and a $C_{5+}$ gasoline hydrocarbons).

14 Claims, 3 Drawing Sheets

(51) Int. Cl.
C07C 7/09 (2006.01)
C10G 63/04 (2006.01)

(52) U.S. Cl.
CPC ...... C07C 2523/28 (2013.01); C07C 2523/30 (2013.01); C07C 2523/36 (2013.01); C07C 2529/08 (2013.01); C07C 2529/40 (2013.01); C10G 2300/1081 (2013.01); C10G 2400/02 (2013.01)

(56) References Cited

U.S. PATENT DOCUMENTS

| | | | |
|---|---|---|---|
| 4,119,678 A | 10/1978 | Neuzil et al. | 585/366 |
| 4,455,445 A | 6/1984 | Neuzil et al. | 585/820 |
| 4,718,986 A | 1/1988 | Comiotto et al. | 203/26 |
| 4,830,729 A | 3/1989 | Dessau et al. | 208/89 |
| 6,075,173 A | 6/2000 | Chodorge et al. | 585/324 |
| 6,271,430 B2 | 8/2001 | Schwab et al. | 585/644 |
| 6,307,117 B1 * | 10/2001 | Tsunoda | C07C 4/06 585/651 |
| 6,683,019 B2 | 1/2004 | Gartside et al. | 502/241 |
| 6,867,341 B1 | 3/2005 | Abrevaya et al. | 585/650 |
| 7,214,841 B2 | 5/2007 | Gartside et al. | 585/324 |
| 7,728,185 B2 | 6/2010 | Senetar et al. | 585/324 |
| 8,153,851 B2 | 4/2012 | Gartside et al. | 585/324 |
| 8,293,961 B2 | 10/2012 | Choi et al. | 585/651 |
| 8,324,441 B2 | 12/2012 | Wegerer et al. | 585/648 |
| 2005/0014981 A1 | 1/2005 | Gartside et al. | 585/324 |
| 2010/0048971 A1 | 2/2010 | Kim et al. | 585/809 |
| 2012/0071701 A1 | 3/2012 | Glover | 585/324 |
| 2014/0014555 A1 | 1/2014 | Marri et al. | 208/78 |

FOREIGN PATENT DOCUMENTS

| | | |
|---|---|---|
| CN | 1852878 A | 10/2006 |
| CN | 100554229 C | 10/2009 |
| EP | 0150544 A1 | 8/1985 |
| EP | 0421701 A1 | 10/1990 |
| EP | 2660288 A1 | 11/2013 |
| WO | WO2003076371 A1 | 9/2003 |
| WO | WO2006098712 A1 | 9/2006 |
| WO | WO2008120921 A1 | 10/2008 |
| WO | WO2013016660 A1 | 1/2013 |

* cited by examiner

FIG. 3 ial Patent Application No. 62/437,306 filed Dec. 21, 2016. The entire contents of each of the above-referenced disclosures is specifically incorporated by reference herein without disclaimer.

PROCESS TO PRODUCE OLEFINS FROM A CATALYTICALLY CRACKED HYDROCARBONS STREAM

CROSS REFERENCE TO RELATED APPLICATIONS

This application is a national phase application under 35 U.S.C. § 371 of International Application No. PCT/IB2017/057968 filed Dec. 14, 2017, which claims priority to U.S. Provisional Patent Application No. 62/437,306 filed Dec. 21, 2016. The entire contents of each of the above-referenced disclosures is specifically incorporated by reference herein without disclaimer.

BACKGROUND OF THE INVENTION

A. Field of the Invention

The invention generally concerns the production of olefins from catalytic cracking of alkane (paraffinic) hydrocarbons. In particular, the invention concerns catalytically cracking a hydrocarbons stream that includes $C_5$ and $C_6$ hydrocarbons to produce a mixed butenes stream, which can be converted via self-metathesis into methane, ethylene, propylene, and $C_5+$ gasoline hydrocarbons.

B. Description of Related Art

The conversion of hydrocarbons such as light naphtha into light olefins via catalytic cracking produces commercially valuable $C_2$ to $C_3$ olefins and less valuable olefins such as n-butenes and iso-butenes ("mixed butenes"). To increase the value of the mixed butenes, conventional processes combine the mixed butenes with liquid propane gas (LPG) and sell the combined stream as LPG. Other methods to increase the value of the mixed butene stream is to process the $C_4$ hydrocarbons into $C_5$ olefins that can be further cracked to produce propylene and ethylene. By way of example, U.S. Pat. No. 7,728,185 to Senetar et al. describes a process to increase the propylene yield from a hydrocarbon cracking unit. The process includes separating a $C_4$ stream into a normal butane stream containing n-butane and 2-butene, and an iso-butane stream containing iso-butane, iso-butene, and 1-butene. The iso-butane stream is passed to an alkylation reactor to dimerize some of the iso-butane stream to form larger hydrocarbons having 8 or more carbon atoms. The larger hydrocarbons are readily separated from unreacted $C_4$ hydrocarbons and are passed to an olefin cracking unit to produce ethylene and propylene.

While various attempts to increase ethylene and propylene production and to utilize the $C_4$ stream from a hydrocarbon cracking process have been described, there is still a need to utilize the $C_4$ stream produced from a hydrocarbon cracking processes in a cost effective and efficient manner.

SUMMARY OF THE INVENTION

An alternate process to increase the production of more economically desired products from a mixed $C_4$ hydrocarbons stream (e.g., n-butene and iso-butene mixture) produced from a hydrocarbon catalytic cracking process has been developed. The process is premised on subjecting the mixed $C_4$ hydrocarbons stream obtained from a hydrocarbon catalytic cracking process to self-metathesis conditions under conditions sufficient to produce $C_5+$ gasoline hydrocarbons and $C_{1-3}$ hydrocarbons. The process successfully integrates the hydrocarbon cracking process with a self-metathesis of $C_4$ hydrocarbons to produce more economically viable products, notably, gasoline hydrocarbons, methane, ethylene, and propylene.

Embodiments of the present invention describe processes for producing olefins. A process can include: (a) catalytically cracking a hydrocarbons stream comprising $C_5$ and $C_6$ hydrocarbons under conditions sufficient to form a first stream comprising $C_5+$ gasoline hydrocarbons, $C_1$ to $C_4$ hydrocarbons, (b) fractionating the first stream to produce at least a (1) first stream comprising $C_5+$ gasoline hydrocarbons, and (2) a gaseous stream comprising the $C_1$ to $C_4$ hydrocarbons and residual $C_5+$ hydrocarbons; (c) separating the gaseous stream into a gaseous mixed $C_4$ hydrocarbons stream comprising n-butene and iso-butene, a gaseous $C_3$ hydrocarbons stream, and a second $C_5+$ gasoline hydrocarbons stream; (d) contacting the mixed $C_4$ gaseous stream with a metathesis catalyst under conditions sufficient to produce a second gaseous stream comprising methane, ethylene and/or propylene, and a product stream comprising $C_5+$ gasoline hydrocarbons; and (e) mixing the step (d) second gaseous stream with the step (c) gaseous stream. The separated second $C_5+$ gasoline hydrocarbons stream can be mixed with the $C_5+$ gasoline hydrocarbons product stream.

The step (c) separation can include (i) producing a gaseous product stream comprising $C_1$ and $C_2$ hydrocarbons and a gaseous $C_3+$ hydrocarbons stream that can include the gaseous mixed $C_4$ hydrocarbons, the gaseous $C_3$ hydrocarbons, and the residual $C_5+$ gasoline hydrocarbons; and (ii) separating the gaseous $C_3+$ hydrocarbons stream into a gaseous $C_3$ hydrocarbons stream, a gaseous mixed $C_4$ hydrocarbons stream comprising n-butene and iso-butene, and the $C_5+$ gasoline hydrocarbons stream. In some embodiments, the gaseous $C_3+$ hydrocarbons stream can be separated into a gaseous $C_3/C_4$ stream and the $C_5+$ gasoline hydrocarbons stream. The gaseous $C_3/C_4$ stream can be separated into the gaseous $C_3$ hydrocarbons stream and a gaseous mixed $C_4$ hydrocarbons stream that includes the n-butene and iso-butene, which can be provided to the step (c) metathesis reaction. In certain instances the gaseous mixed $C_4$ hydrocarbons stream can include $C_4$ acyclic alkanes and the $C_4$ hydrocarbons stream, and can be separated into a $C_4$ olefins stream that includes the n-butene and the iso-butene and a $C_4$ acyclic alkanes stream. The $C_4$ olefins stream can be provided to the metathesis reaction of step (d).

In some embodiments, the second gaseous stream of step (d) can include $C_4$ hydrocarbons. Embodiments of the process can include separating the separating the second gaseous stream into a gaseous $C_{1-3}$ hydrocarbons stream and a $C_4$ hydrocarbons stream and mixing the gaseous $C_{1-3}$ hydrocarbons stream with the step (c) gaseous stream. The $C_4$ hydrocarbons stream can be separated into a $C_4$ olefins stream and a $C_4$ acyclic alkane stream and providing the $C_4$ olefins stream to step (d).

Embodiments of the catalytic hydrocarbon cracking conditions can include contacting the hydrocarbons stream with a catalyst at a catalyst to hydrocarbon ratio of 3:1 to 40:1. In some embodiments, the contacting can be performed in the presence of water, steam, or both. The conditions can also include a temperature of 500-700° C. and/or a pressure of 0.05 MPa to 0.5 MPa. In some embodiments, the catalyst can include an acidic catalyst. The acidic catalyst can be a zeolite catalyst such as a medium pore zeolite catalyst (e.g., a ZSM-5, a modified ZSM-5 or a mixture of both), a large pore catalyst (e.g., a Y zeolite, an ultra-stable zeolite Y or a mixture of both), or a mixture of both. In certain embodiments, step (a) can be performed in a catalytic cracker unit comprising a fixed catalyst bed, a moving catalyst bed, or fluidized catalyst bed.

Embodiments of step (c) of the process can include a temperature of 200 to 550° C. and/or a pressure of 0.1 MPa to 2.0 MPa. A metathesis catalyst can include a Column 6 metal (e.g., tungsten (W), or molybdenum (Mo)) or compound thereof, a noble metal (e.g., rhodium (Rh)) or a compound thereof, or a combination thereof.

The following includes definitions of various terms and phrases used throughout this specification.

The term "catalyst" means a substance which alters the rate of a chemical reaction. "Catalytic" or "catalytically active" means having the properties of a catalyst.

The term "cracking" means to break a carbon-carbon bond of a hydrocarbon molecule to produce a hydrocarbon having fewer carbon atoms than the starting hydrocarbon molecule.

The term "gasoline hydrocarbons" refers to a hydrocarbons stream containing hydrocarbons having up to 12 carbons suitable to be made into gasoline. For example, $C_5+$ gasoline hydrocarbons refer to a hydrocarbons stream having $C_5$ to $C_{12}$ hydrocarbons.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The processes of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the processes of the present invention are their abilities to produce $C_2$ and $C_3$ hydrocarbons and a $C_5+$ hydrocarbons stream from a mixed $C_4$ stream produced from catalytically cracking a $C_{5-6}$ hydrocarbons stream.

In the context of the present invention, twenty embodiments are now described. Embodiment 1 is a process for producing olefins. The process includes the steps of (a) catalytically cracking a hydrocarbons stream containing $C_5$ and $C_6$ hydrocarbons under conditions sufficient to form a cracked hydrocarbons stream containing $C_5+$ gasoline hydrocarbons, and gaseous $C_1$ to $C_4$ hydrocarbons; (b) fractionating the first stream to produce at least (1) a first stream containing $C_5+$ gasoline hydrocarbons, and (2) a gaseous stream containing the $C_1$ to $C_4$ hydrocarbons and residual $C_5+$ hydrocarbons; (c) separating the gaseous stream into a gaseous mixed $C_4$ hydrocarbons stream containing n-butene and iso-butene, a gaseous $C_3$ hydrocarbons stream, and a $C_5+$ gasoline hydrocarbons stream; (d) contacting the mixed $C_4$ gaseous stream with a metathesis catalyst under conditions sufficient to produce a second gaseous stream containing methane, ethylene and/or propylene, and a product stream containing $C_5+$ gasoline hydrocarbons; and (e) mixing the step (d) second gaseous stream with the step (c) gaseous stream. Embodiment 2 is the process of embodiment 1, further containing mixing the $C_5+$ gasoline hydrocarbons product stream with the $C_5+$ gasoline hydrocarbons stream. Embodiment 3 is the process of any one of embodiments 1 to 2, wherein separating the gaseous stream of step (c) includes the steps of (i) producing a gaseous product stream containing $C_1$ and $C_2$ hydrocarbons and a gaseous $C_3+$ hydrocarbons stream containing the gaseous mixed $C_4$ hydrocarbons, the gaseous $C_3$ hydrocarbons, and the residual $C_5+$ gasoline hydrocarbons; and (ii) separating the gaseous $C_3+$ hydrocarbons stream into a gaseous $C_3$ hydrocarbons stream, a gaseous mixed $C_4$ hydrocarbons stream containing n-butene and iso-butene, and the second $C_5+$ gasoline hydrocarbons stream. Embodiment 4 is the process of embodiment 3, further containing separating the $C_3+$ hydrocarbons stream into a gaseous $C_3/C_4$ stream and the second $C_5+$ gasoline hydrocarbons stream. Embodiment 5 is the process of embodiment 4, further containing separating the gaseous $C_3/C_4$ stream into the gaseous $C_3$ hydrocarbons stream and the gaseous mixed $C_4$ hydrocarbons stream containing the n-butene and the iso-butene. Embodiment 6 is the process of embodiment 5, wherein the gaseous mixed $C_4$ hydrocarbons stream contains $C_4$ acyclic hydrocarbons and the process further includes the step of separating the gaseous mixed $C_4$ hydrocarbons stream into a $C_4$ olefins stream and a $C_4$ acyclic alkanes stream, and providing the $C_4$ olefins stream to step (d). Embodiment 7 is the process of any one of embodiments 1 to 6, wherein the second gaseous stream of step (d) contains $C_4$ hydrocarbons. Embodiment 8 is the process of embodiment 7, wherein the process includes separating the second gaseous stream into a gaseous $C_{1-3}$ hydrocarbons stream and a $C_4$ hydrocarbons stream and mixing the gaseous $C_{1-3}$ hydrocarbons stream with the step (c) gaseous stream. Embodiment 9 is the process of embodiment 8, further including the step of separating the $C_4$ hydrocarbons stream into a $C_4$ olefins stream and a $C_4$ acyclic alkane stream and providing the $C_4$ olefins stream to step (d). Embodiment 10 is the process of any one of embodiments 1 to 9, wherein the step (a) conditions include contacting the hydrocarbons stream with a catalyst at a catalyst to hydrocarbon ratio of 3:1 to 40:1. Embodiment 11 is the process of any one of embodiments 1 to 10, wherein the catalytic cracking conditions include a temperature of 500-700° C. and a pressure of 0.05 MPa to 0.5 MPa. Embodiment 12 is the process of any one of embodiments 1 to 11, wherein the catalytic cracking conditions include an acidic catalyst. Embodiment 13 is the process of embodiment 12, wherein the acidic catalyst contains a medium pore zeolite catalyst, a large pore catalyst, or a mixture of both. Embodiment 14 is the process of embodiment 13, wherein the medium pore zeolite catalyst is a ZSM-5, a modified ZSM-5 or a mixture of both and the large pore zeolite catalyst is a Y zeolite, an ultra-stable zeolite Y, or a mixture of both. Embodiment 15 is the process of any one of embodiments 1 to 14, wherein the step (a) is performed in a catalytic cracker unit including a fixed catalyst bed, a moving catalyst bed, or fluidized catalyst bed. Embodiment 16 is the process of any one of embodiments 1 to 15, wherein the catalytic cracking conditions include water, steam or both. Embodiment 17 is the process of any one of embodiments 1 to 16, wherein the step (d) metathesis conditions include a temperature of 200 to 550° C. and a pressure of 0.1 MPa to 2.0 MPa. Embodiment 18 is the process of any one of embodiments 1 to 17, wherein the step (d) catalyst includes a Column 6 metal or compound thereof, a noble metal or a compound thereof, or a combination thereof. Embodiment 19 is the process of embodiment 18, wherein the Column 6 metal is tungsten, molybdenum, or both. Embodiment 20 is the process of any one of embodiments 18 to 19, wherein the noble metal is rhenium.

Other objects, features, and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

While the invention is susceptible to various modifications and alternative forms, specific embodiments thereof are shown by way of example in the drawings. The drawings may not be to scale.

DETAILED DESCRIPTION OF THE INVENTION

An alternate process to produce $C_5$+ gasoline hydrocarbons and methane, ethylene propylene from a gaseous stream produced from catalytically cracking of a $C_{5-6}$ hydrocarbons stream has been discovered. The process successfully integrates a self-metathesis of $C_4$ hydrocarbons process into a catalytically cracking of hydrocarbons process to produce more commercially valuable products from a mixed $C_4$ hydrocarbons stream. The mixed $C_4$ hydrocarbons stream used in this process can be produced from the aforementioned hydrocarbon catalytic cracking reaction, thereby providing a sustainable process for value added commercial products such as methane, ethylene, propylene and $C_5$+ hydrocarbons.

These and other non-limiting aspects of the present invention are discussed in further detail in the following sections with reference to the figures.

Figure 1A:
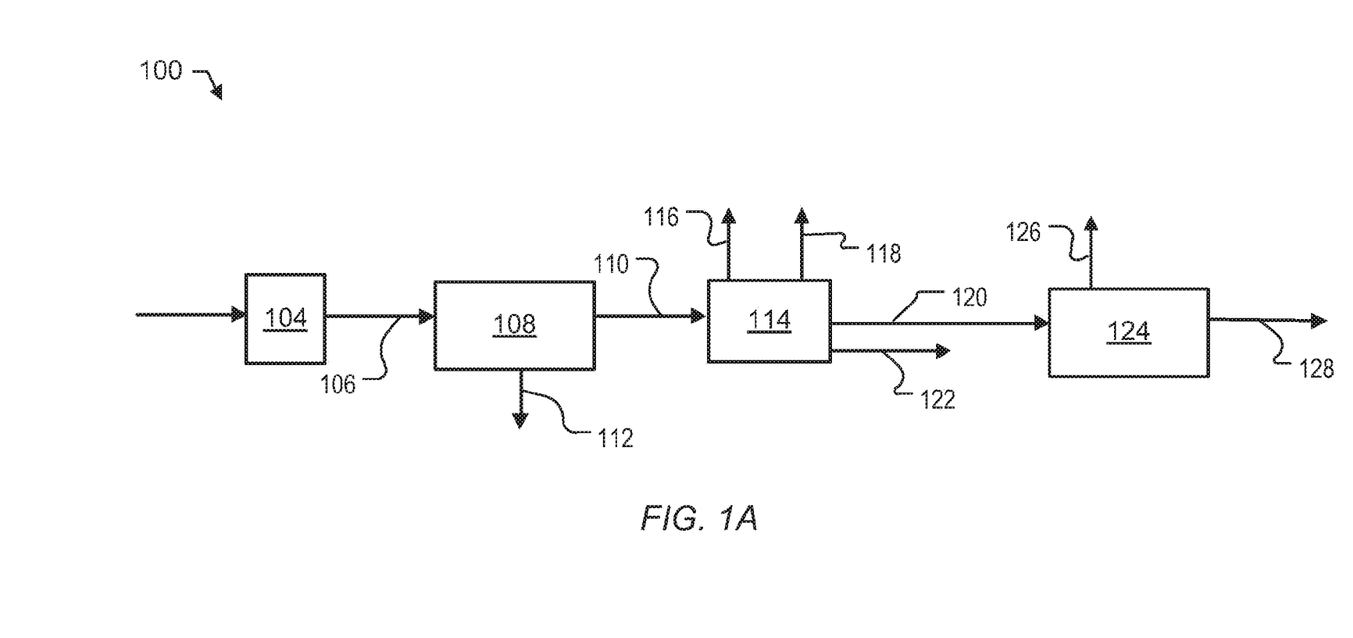
FIGS. 1A and 1B depict schematics of a process of the present invention to produce $C_{1-2}$ hydrocarbons, $C_3$ hydrocarbons, mixed $C_4$ hydrocarbons and $C_5$+ gasoline hydrocarbons from a catalytically cracked hydrocarbons stream.
Figure 1B:
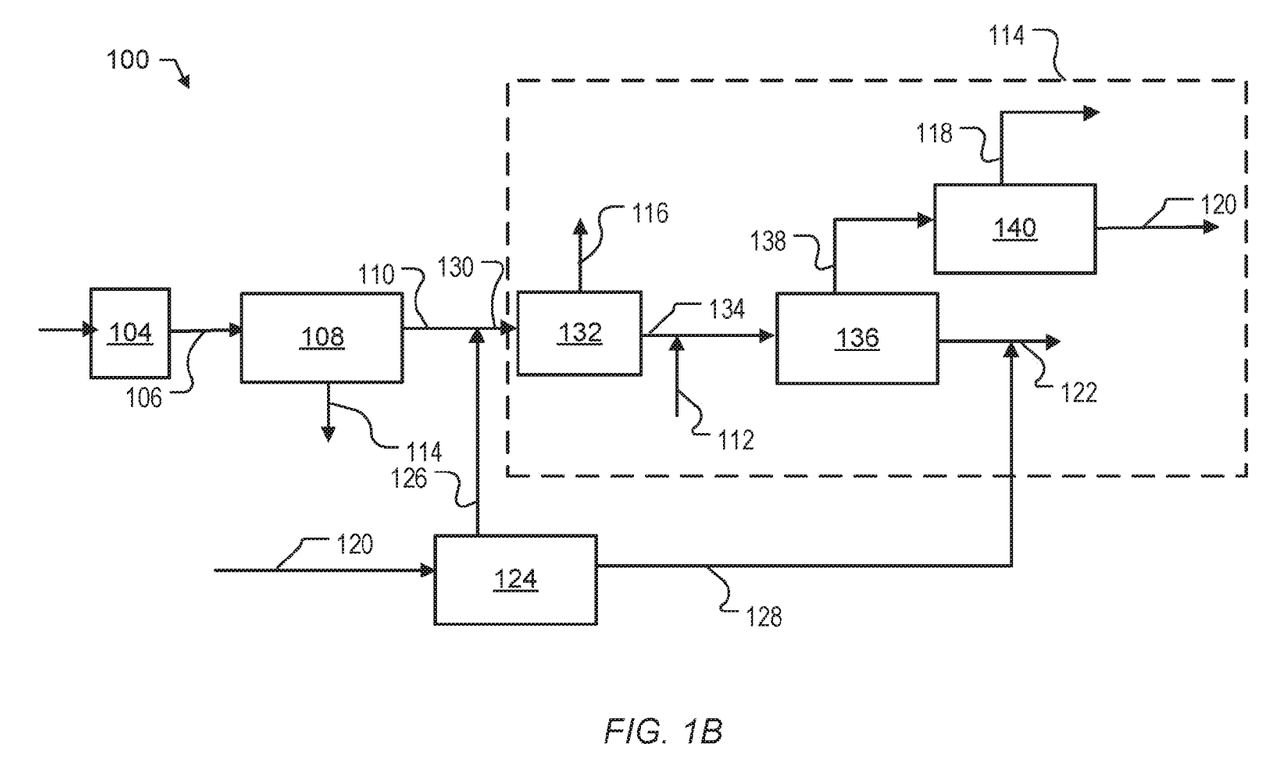
Figure 2:
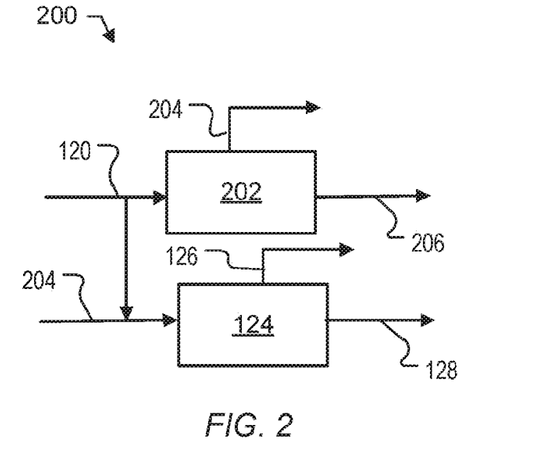
FIG. 2 depicts a schematic of a process of the present invention to produce $C_4$ olefins, $C_4$ acyclic alkanes, and $C_5$+ gasoline hydrocarbons from a catalytically cracked hydrocarbons stream.
Figure 3:
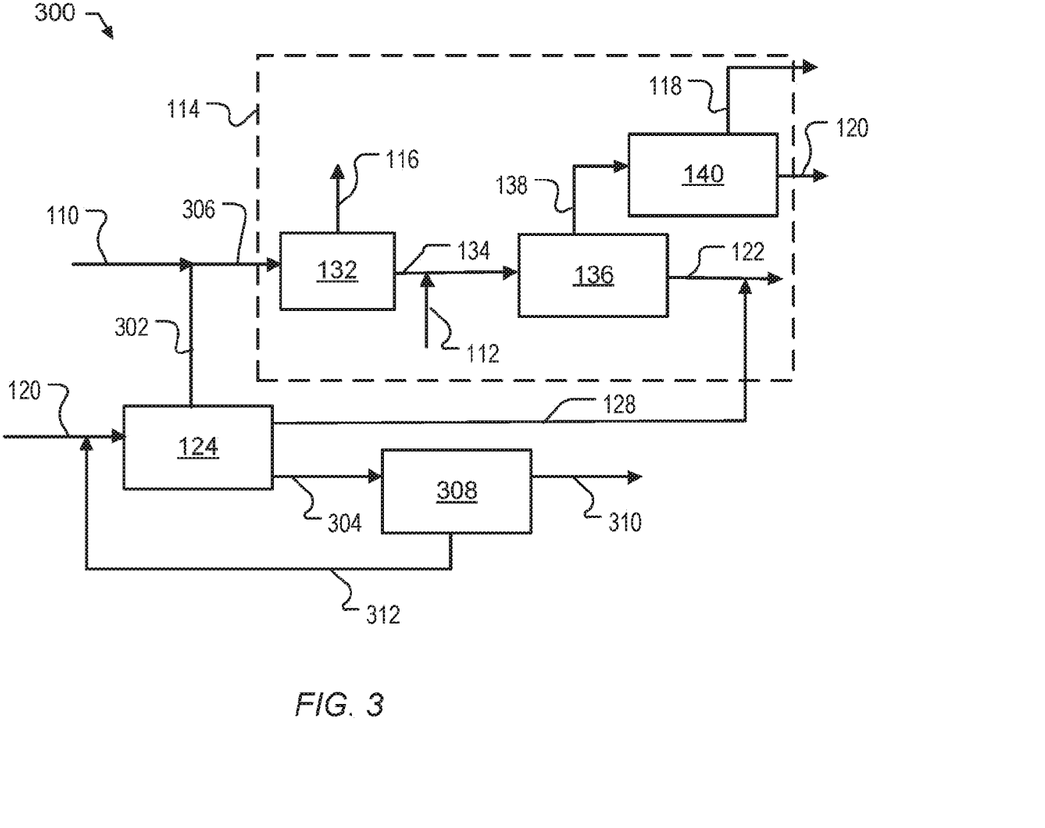
FIG. 3 depicts a schematic of a process of the present invention to produce mixed $C_4$ hydrocarbons, $C_5$+ gasoline hydrocarbons, and acyclic alkanes from a catalytically cracked hydrocarbons stream.

FIGS. 1A, 1B, 2, and 3 depict processes to produce $C_3$ olefins and $C_5$+ gasoline hydrocarbons from a mixed $C_4$ hydrocarbons stream and/or a $C_4$ olefins stream produced from a catalytically cracked hydrocarbons stream. FIGS. 1A and 1B depict schematics of process 100 of the present invention to produce mixed $C_4$ hydrocarbons and $C_5$+ gasoline hydrocarbons from a catalytically cracked hydrocarbons stream. FIG. 2 depicts a schematic of process 200 of the present invention to produce $C_4$ olefins, $C_4$ acyclic alkanes, and $C_5$+ gasoline hydrocarbons from a catalytically cracked hydrocarbons stream. FIG. 3 depicts a schematic of process 300 of the present invention to produce mixed $C_4$ hydrocarbons, $C_5$+ gasoline hydrocarbons, and acyclic alkanes from a catalytically cracked hydrocarbons stream. Referring to the FIGS., hydrocarbons stream 102 can enter catalytic cracking unit 104. Hydrocarbons stream 102 can include a mixture of hydrocarbons having 5 to 28 carbon atoms ($C_5$ to $C_{28}$ hydrocarbons). Hydrocarbons stream 102 can have a boiling point between 30° C. and 315° C. and can include straight chain acyclic alkanes (paraffins), cyclic alkanes (naphthenes), aromatic hydrocarbons, and mixtures thereof. In some embodiments, hydrocarbons stream 102 can be hydrocarbons stream that has a $C_5$ to $C_7$ hydrocarbons and a boiling point from 30° C. to 90° C. In some embodiments, hydrocarbons stream 102 can include 25 to 30 vol. % n-pentane, 10 to 15 vol. % iso-pentane, 1 to 5 vol. % cyclopentane, 20 to 30 vol. % n-hexane, 20 to 35 vol. % iso-hexane, 0.5 to 2 vol. % benzene, 0.01 to 1 vol. % $C_7$ hydrocarbons. A non-limiting example of a $C_5$ to $C_7$ hydrocarbons stream is light naphtha. In some embodiments, hydrocarbons stream 102 can be a $C_5$ to $C_{28}$ hydrocarbons stream, a $C_5$ to $C_{15}$ hydrocarbons stream, a $C_6$ to $C_{16}$ hydrocarbons stream, $C_{10}$ to $C_{28}$ hydrocarbons stream or any mixture thereof. In some embodiments, the catalytic cracking can be performed in the presence of water and/or a steam/water mixture. Hydrocarbons stream 102 can be mixed with steam/water prior to entering catalytic cracking unit 104. In certain embodiments, steam/water can be added directly to catalytic cracking unit 104. Water/steam can be added in amounts of 20 wt. % to 30 wt. %, or about 25 wt. %.

In catalytic cracking unit 104, hydrocarbons stream 102 can be contacted with a hydrocracking catalyst under conditions suitable to produce a cracked hydrocarbons stream 106. Cracked hydrocarbons stream 106 can include $C_5$+ gasoline hydrocarbons and gaseous $C_1$ to $C_4$ ($C_{1-4}$) hydrocarbons. Catalytic cracking unit 102 can be any unit capable of cracking hydrocarbons into smaller molecular weight hydrocarbons (i.e., having a lower carbon number than hydrocarbons stream 102). Non-limiting examples of catalytic cracking units include a fixed catalyst bed catalytic cracker, a moving catalyst bed catalytic cracker, or fluidized catalyst bed catalytic cracker. In embodiments when a fluidized bed catalytic cracker is used, the hydrocarbons stream can flow through the catalyst bed in an upwardly or downwardly direction. The hydrocracking catalyst used for cracking the hydrocarbons stream can be an acidic catalyst. Acidic hydrocracking catalysts can include medium pore zeolites, large pore zeolites, and mixtures thereof. Non-limiting examples of medium pore zeolites can include ZSM-5, modified ZSM-5, spray dried ZSM-5, spray dried modified ZSM-5 and the like. Non-limiting examples of large pore zeolite catalyst can include a Y zeolite, an ultra-stable zeolite Y or a mixture of both. Zeolite catalysts can be obtained from commercial vendors such as Grace Catalysts Technologies (U.S.A.), Sigma-Aldrich® (U.S.A.), or Zeolyst International, (U.S.A.). Contacting conditions can include temperature, pressure, residence time and the like. Average temperatures in catalytic cracking unit 104 can range from 500° C. to 700° C., 525° C. to 625° C., 550° C. to 600° C., or any value or range there between. Average pressures in catalytic cracking unit 104 can range from 0.1 MPa to 2 MPa, or 0.5 to 1.5 MPa, or 0.75 to 1.0 MPa or any value or range there between. In embodiments when a fluidized bed catalytic cracker is used, a residence time of hydrocarbons stream 102 in the fixed catalyst bed can be 1 to 10 seconds, or 2 to 9 seconds, or 3 to 8 seconds, or any value or range there between. In a non-limiting example, a $C_{5-6}$ hydrocarbons stream can be contacted with a zeolite catalyst and 25 wt. % steam in a fluidized bed reactor at a temperature of 650 to 690° C. to produce first hydrocarbons stream 106 and second hydrocarbons stream 108.

Cracked hydrocarbons stream 106 can exit catalytic cracking unit 104 and enter fractionation unit 108. In fractionation unit 108, cracked hydrocarbons stream 106 can be separated into a plurality of streams that can include gaseous hydrocarbons stream 110 and $C_5$+ gasoline hydrocarbons stream 112. In some embodiments, $C_5$+ gasoline hydrocarbons stream 112 can be recycled to catalytic cracking unit 104. Other streams (not shown) that can be produced from fractionation unit 108 include light and heavy cycle oil, heavy hydrocarbons, coke, and the like. The other streams can be sold, transported, recycled, or sent to other processing units. Fractionation unit 108 can be any fractionation unit known in the art capable of separating a hydrocarbons stream. Fractionation unit can include one or more units, one or more distillation plates, etc.

Gaseous hydrocarbons stream 110 can include from $C_1$ to $C_4$ hydrocarbons (e.g., methane, ethane, propane, butane, n-butene and iso-butene, propylene, ethane, or mixtures thereof) and residual $C_5$+ gasoline hydrocarbons. Gaseous hydrocarbons stream 110 can enter gas separation unit 114 and be subjected to conditions to sufficient to hydrocarbons into gaseous $C_{1-2}$ hydrocarbon steam 116, gaseous $C_3$ hydrocarbons stream 118, gaseous mixed $C_4$ hydrocarbons stream 120, and $C_5$+ gasoline hydrocarbons stream 122. Gas separation unit 114 can include one or more cryogenic distillation units, membrane units, debutanizers, de-ethanizers, or any known separation unit capable of separating hydrocarbons. Gaseous $C_{1-2}$ hydrocarbon steam 116 can include methane and/or $C_2$ hydrocarbons, preferably ethylene and ethane. In some embodiments, gaseous $C_{1-2}$ hydrocarbon steam contains none or substantially no methane. Gaseous $C_3$ hydrocarbons stream can include propylene and propane. Gaseous $C_{1-2}$ hydrocarbon steam 116 and/or gaseous $C_3$ hydrocarbons stream can exit gaseous separation unit 114 and be stored, transported, sold, or provided to other processing units. Second $C_5$+ gasoline hydrocarbons stream 122 can be stored, sold, transported to other processing units to be additized or further processed for use as gasoline, combined with other $C_5$+ gasoline hydrocarbons streams, or combinations thereof. Mixed $C_4$ hydrocarbons stream 120 can include $C_4$ alkanes and $C_4$ olefins. In some embodiments, mixed $C_4$ hydrocarbons stream includes 0 to 100 vol. % n-butene and/or 0 to 100 vol. % iso-butene.

Mixed $C_4$ hydrocarbons stream 120 that includes n-butene and iso-butene (mixed butenes) can exit separation unit 114 and enter $C_4$ metathesis unit 124. In $C_4$ metathesis unit 124, mixed $C_4$ hydrocarbons stream 120 can be contacted with a catalyst under conditions sufficient to produce gaseous product stream 126 and product stream 128 that includes $C_5$+ gasoline hydrocarbons. Gaseous product stream 126 can includes $C_{2-4}$ olefins (e.g., ethylene, propylene, butylene, or mixtures thereof) and methane. The conversion of mixed butenes to $C_5$+ hydrocarbons can be shown in the following chemical equations:

$$1\text{-}C_4H_8 + 2\text{-}C_4H_8 \rightarrow C_3H_6 + 2\text{-}C_5H_{10} \tag{1}$$

$$\text{Iso-}C_4H_8 + 2\text{-}C_4H_8 \rightarrow C_3H_6 + H_3C\text{—}C(CH_3)\text{=}C(H)\text{—}CH_2\text{—}CH_3 \tag{2}$$

$$\text{Iso-}C_4H_8 + 1\text{-}C_4H_8 \rightarrow C_2H_4 + H_3C\text{—}C(CH_3)\text{=}C(H)\text{—}CH_2\text{—}CH_3 \tag{3}$$

$$1\text{-}C_4H_8 + 1\text{-}C_4H_8 \rightarrow C_2H_4 + 3\text{-}C_6H_{12} \tag{4}$$

Other reactions such as oligomerization, cracking, self-metathesis of isobutylene and isomerization of normal butenes can also occur in $C_4$ metathesis unit 124. Conditions sufficient to convert the n-butene and iso-butene hydrocarbons into higher molecular weight (i.e., higher carbon number) compounds include a temperature of 200° C. to 550° C., 250° C. to 500° C., 300° C. to 450° C., or 400° C. to 450° C. or any value or range there between and a pressure of 0.1 MPa to 2.0 MPa, 0.5 MPa to 1.5 MPa, or any value or range there between. The catalyst in metathesis unit 116 can be any catalyst capable of catalyzing a $C_4$ metathesis reaction. The metathesis catalyst can include a metal from Column 6 of the Periodic Table (e.g., W or Mo) or compounds thereof and/or a noble metal (e.g., Rh) or compounds thereof. In a preferred aspect, the catalyst can be W/Rh or Mo/Rh. Non-limiting examples of metathesis catalysts are described in U.S. Pat. No. 6,683,019 to Gartside et al., or can be obtained from commercial vendors such as Aperion synthesis (Poland) or Sigma-Aldrich® (U.S.A.).

Referring to FIG. 1B, gaseous product stream 126 can exit $C_4$ metathesis unit 124 and be combined with gaseous hydrocarbons stream 110 to form mixed gaseous stream 130. Mixed gaseous stream can include from $C_1$ to $C_4$ hydrocarbons (e.g., methane, ethane, propane, butane, n-butene and iso-butene, propylene, ethane, or mixtures thereof). Mixed gaseous stream 130 can enter gas separation unit 132 of separation unit 114 and be subjected to conditions sufficient to separate $C_{1-2}$ hydrocarbons from $C_3$+ hydrocarbons and produce gaseous $C_{1-2}$ hydrocarbons stream 116 and gaseous $C_3$+ hydrocarbons stream 134. Gas separation unit 132 can be a cryogenic distillation unit, a membrane unit, or any known separation unit capable of separating $C_{1-4}$ hydrocarbons. Gaseous $C_{1-2}$ hydrocarbons 116 can include methane and/or $C_2$ hydrocarbons. Gaseous $C_{1-2}$ hydrocarbons 116 can exit gaseous separation unit 124 and be stored, transported, sold, or provided to other processing units. Gaseous $C_3$+ hydrocarbons stream 134 can include $C_3$+ hydrocarbons and can be mixed with $C_5$+ gasoline hydrocarbons stream 112 and enter debutanizer unit 136. In some embodiments, the streams are not mixed, but enter the debutanizer separately and are mixed in the debutanizer unit 136. In debutanizer unit 136, the mixed $C_3$+ hydrocarbons stream can be subjected to conditions sufficient to separate the stream into $C_{3-4}$ hydrocarbons stream 138 and $C_5$+ gasoline hydrocarbons stream 122. $C_5$+ gasoline hydrocarbons stream 122 can be stored, sold, mixed with other $C_5$+ hydrocarbons streams, transported to other processing units to be additized and/or further processed for use as gasoline, or combinations thereof. As shown, $C_5$+ gasoline hydrocarbons product stream 128 is mixed with $C_5$+ gasoline hydrocarbons stream 122. In some embodiments, the two streams are not mixed. $C_{3-4}$ hydrocarbons stream 138 can enter de-ethanizer unit 140 and be separated into $C_3$ hydrocarbons stream 118 and mixed $C_4$ hydrocarbons stream 120. $C_3$ hydrocarbons stream can include propylene and propane. $C_3$ hydrocarbons stream can exit de-ethanizer unit 140 and be sold (LPG), transported, stored, or used in other processing units. Mixed $C_4$ hydrocarbons stream 120 can include $C_4$ alkanes and $C_4$ olefins. Mixed $C_4$ hydrocarbons stream 120 can exit debutanizer unit 140 and be stored, sold, transported, or provided to other processing units such as metathesis unit 124.

Referring to FIG. 2, separation unit 114 includes a $C_4$ separation unit 202. Mixed $C_4$ hydrocarbons stream 120 from de-ethanizer unit 140 (See, FIGS. 1A and 1B) can enter $C_4$ separation unit 202 and be separated into $C_4$ olefins stream 204 and $C_4$ paraffins stream 206. $C_4$ olefins stream 204 can exit $C_4$ separations unit 202 and be provided to metathesis unit 124 or be sold, transported, or stored. In some embodiments, a portion of mixed $C_4$ hydrocarbons stream 120 is provided to $C_4$ separation unit 202 and a portion of the mixed $C_4$ hydrocarbons stream is sent to metathesis unit 124. $C_4$ olefins stream 204 is mixed with a portion of the mixed $C_4$ hydrocarbons stream and be provided to metathesis unit 116. $C_4$ paraffins stream 206 can be stored, transported, sold, or provided to other processing units.

Referring to FIG. 3, metathesis unit 116 can be configured to produce a $C_{1-3}$ hydrocarbons stream 302, a $C_4$+ hydrocarbons stream 304, and $C_5$+ hydrocarbons stream 120. By way of example, metathesis unit 124 can include one or more separation units coupled to the metathesis reactor. In some embodiments, metathesis unit 124 produces a $C_{1-3}$ hydrocarbons stream and a $C_4$+ hydrocarbons stream (not shown). The $C_4$+ hydrocarbons stream can be separated into $C_4$ hydrocarbons stream 304 and $C_5$+ gasoline hydrocarbons stream 306. In certain embodiments, metathesis unit 124 produces a $C_{1-4}$ hydrocarbons stream (not shown) and a $C_5$+ hydrocarbons stream (not shown). The $C_{1-4}$ hydrocarbons stream can be separated into $C_4$ hydrocarbons stream 304 and $C_{1-3}$ hydrocarbons stream 302. $C_{1-3}$ hydrocarbons stream can exit metathesis unit 124 and be combined with gaseous stream 110 to form combined (mixed) gaseous stream 306 and enter gas separation unit 132. In gas separation unit 132, the gaseous stream can be subjected to conditions sufficient to separate $C_{1-2}$ hydrocarbons from $C_{3-4}$ hydrocarbons and produce $C_{1-2}$ hydrocarbons 116 and gaseous $C_3$+ hydrocarbons stream 134. First gaseous stream 126 can include methane and/or $C_2$ hydrocarbons. Gaseous $C_3$+ hydrocarbons stream 134 can include $C_3$ and/or $C_4$ hydrocarbons. $C_5$+ hydrocarbons product stream 128 can be combined with $C_5$+ hydrocarbons stream 122 to form a mixed $C_5$+ hydrocarbons stream as previously described for FIGS. 1 and 2. $C_4$ hydrocarbons stream 304 can exit metathesis unit 124 and enter $C_4$ separation unit 308. In separation unit 308, $C_4$ hydrocarbons stream 304 is subjected to conditions sufficient to separate the $C_4$ hydrocarbons stream into a $C_4$ acyclic alkane (paraffinic) stream 310 and a $C_4$ olefin stream 312. $C_4$ separation 308 can be any separation unit capable of separating alkanes from olefins. Non-limiting examples of separation unit 308 include distillation units (See, for example, U.S. Pat. No. 4,718,986 and 2010/0048971) and/or adsorptive units (See, for example, European Patent No. EP0150544, International Patent Application Publication No. WO 2008120921, and U.S. Pat. Nos. 3,723,561; 4,119,678; and 4,455,445). $C_4$ acyclic alkane (paraffinic) stream 310 can be stored, sold, transported, and/or provided to other processing units. $C_4$ olefin stream 312 can be recycled to metathesis unit 124. As shown $C_4$ olefin stream 312 is combined with mixed $C_4$ hydrocarbons stream 120 and provided to metathesis unit 124.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Catalytically Cracking of a $C_{5-6}$ Hydrocarbons Stream

A zeolite catalyst was tested for light naphtha cracking using a fluidized bed pilot plant on a single pass. The light straight run naphtha (LSRN) composition is listed in Table 1. Reactor temperature, steam/feed ratio, and residence time are listed in Table 2. Recycle of $C_5$+ gasoline hydrocarbons stream to the reactor would increase the conversion and yields of light olefins. As can be seen the yields of $C_4$ is around 11.3 wt. %.

TABLE 1

| Feed (LSRN) | |
| --- | --- |
| Component | Wt. % |
| n-pentane | 28.8 |
| iso-pentane | 11.8 |
| cyclopentane | 1.9 |
| n-hexane | 24.5 |
| iso-hexane | 26.9 |
| cyclohexane | 4.6 |
| benzene | 1.3 |
| $C_7$s | 0.3 |
| Sum | 100 |

TABLE 2

| Reaction conditions and Product yields | |
| --- | --- |
| Temperature (° C.) | 670 |
| Steam/Feed (wt. %) | 25 |
| Residence time (seconds) | 5 |
| $C_5$+ gasoline hydrocarbons, wt. % | 34.6 |
| Light cycle oil (LCO) + bottoms, wt. % | 1.1 |
| $C_{1-3}$ alkanes + $H_2$, wt. % | 23 |
| $C_{2-4}$ Olefins, wt. % | 30 |
| $C_4$ total (alkanes and olefins), wt. % | 11.3 |
| Iso-$C_4$ olefins, wt. % | 3.7 |
| n-$C_4$ olefins, wt. % | 5.4% |

Example 2

Simulation of $C_4$ Metathesis Reaction

The self-metathesis reactions of mixed butenes including isobutenes were simulated. The simulation used more than eight reactions. The product distribution is shown in Table 3. It was determined that the yield of $C_{1-3}$ olefins was about 23 wt. %.

TABLE 3

| Component | Feed (wt. %) | Product (wt. %) |
|---|---|---|
| Ethylene | 0.0 | 3.02 |
| propylene | 0.00 | 20.02 |
| 1-$C_4$ olefin | 48.61 | 5.68 |
| Iso-$C_4$ olefin | 32.23 | 9.67 |
| butane | 19.16 | 19.15 |
| Total $C_5$ olefins | 0.00 | 33.38 |
| $C_6$ olefins | 0.00 | 9.07 |

Example 3

Integration of Example 1 with Example 2-Catalytic Cracking and $C_4$ Metathesis

The products from the integration of the catalytic cracking process of Example 1 with the $C_4$ metathesis reaction of Example 2 are shown in Table 4. Inventors:

TABLE 4

| Integration Results | |
|---|---|
| $C_5$+ gasoline hydrocarbons | 39.4 |
| Light cycle oil (LCO) + bottoms, wt. % | 1.1 |
| $C_{1-3}$ alkanes and $H_2$ | 23.0 |
| $C_{2-4}$ olefins, wt. % | 32.6 |
| $C_4$ total | 3.9 |

The invention claimed is:

1. A process for producing olefins, the process comprising:
   (a) catalytically cracking a hydrocarbons stream consisting essentially of $C_5$ and $C_6$ hydrocarbons under conditions sufficient to form a cracked hydrocarbons stream comprising $C_5$+ gasoline hydrocarbons, and gaseous $C_1$ to $C_4$ hydrocarbons;
   (b) fractionating the cracked hydrocarbons stream to produce at least (1) a first stream comprising $C_5$+ gasoline hydrocarbons, and (2) a gaseous stream comprising the $C_1$ to $C_4$ hydrocarbons and residual $C_5$+ hydrocarbons;
   (c) separating the gaseous stream into a gaseous mixed $C_4$ hydrocarbons stream comprising n-butene and iso-butene, a gaseous $C_3$ hydrocarbons stream, and a $C_5$+ gasoline hydrocarbons stream;
   (d) contacting the gaseous mixed $C_4$ hydrocarbons stream with a metathesis catalyst under conditions sufficient to produce a second gaseous stream comprising methane, ethylene and/or propylene, and a product stream comprising $C_5$+ gasoline hydrocarbons; and
   (e) mixing the step (d) second gaseous stream with the step (c) gaseous $C_3$ hydrocarbons stream.

2. The process of claim 1, further comprising mixing the $C_5$+ gasoline hydrocarbons product stream with the $C_5$+ gasoline hydrocarbons stream.

3. The process of claim 1, wherein separating the gaseous stream of step (c) comprises
   (i) producing a gaseous product stream comprising C1 and C2 hydrocarbons and a gaseous C3+ hydrocarbons stream comprising gaseous mixed C4 hydrocarbons, gaseous C3 hydrocarbons, and residual C5+ gasoline hydrocarbons; and
   (ii) separating the gaseous C3+ hydrocarbons stream into the gaseous C3 hydrocarbons stream, the gaseous mixed C4 hydrocarbons stream comprising n-butene and iso-butene, and a second C5+ gasoline hydrocarbons stream.

4. The process of claim 3, wherein the step (a) is performed in a moving catalyst bed.

5. The process of claim 3, wherein the catalytic cracking conditions comprise a temperature of 500-700° C. and a pressure of 0.05 MPa to 0.5 MPa.

6. The process of claim 3, wherein the catalytic cracking conditions comprise an acidic catalyst.

7. The process of claim 6, wherein the acidic catalyst comprises a large pore catalyst.

8. The process of claim 6, wherein acidic catalyst is a Y zeolite, an ultra-stable zeolite Y, or a mixture of both.

9. The process of claim 1, wherein the step (a) is performed in a catalytic cracker unit comprising a fixed catalyst bed, a moving catalyst bed, or fluidized catalyst bed.

10. The process of claim 1, wherein the catalytic cracking conditions comprise water.

11. The process of claim 1, wherein the step (d) metathesis conditions comprise a temperature of 200 to 550° C. and a pressure of 0.1 MPa to 2.0 MPa.

12. The process of claim 1, wherein the step (d) catalyst comprises a Column 6 metal or compound thereof, a noble metal or a compound thereof, or a combination thereof.

13. The process of claim 12, wherein the noble metal is rhenium.

14. The process of claim 1, wherein the step (d) catalyst is molybdenum.

* * * * *